United States Patent
Cabrera et al.

(10) Patent No.: US 6,362,488 B1
(45) Date of Patent: Mar. 26, 2002

(54) LIGHT SOURCE AND METHOD FOR CARRYING OUT LEAK DETECTION INSPECTIONS

(75) Inventors: Robert Cabrera, Hermosa Beach, CA (US); Kenneth J. Kranz, Birmingham; Victor J. Shanley, St. Clair Shores, both of MI (US)

(73) Assignee: Corrosion Consultants, Inc., Roseville, MI (US)

( * ) Notice: Subject to any disclaimer, the term of this patent is extended or adjusted under 35 U.S.C. 154(b) by 0 days.

(21) Appl. No.: 09/491,413

(22) Filed: Jan. 26, 2000

Related U.S. Application Data

(63) Continuation-in-part of application No. 08/964,839, filed on Nov. 5, 1997.

(51) Int. Cl.[7] ............................. G01N 21/64; G01J 1/00
(52) U.S. Cl. .................. 250/459.1; 250/461.1
(58) Field of Search .................. 250/459.1, 461 R, 250/504 R, 504 H, 458.1, 302, 461.1

(56) References Cited

U.S. PATENT DOCUMENTS

| | | | | |
|---|---|---|---|---|
| 4,298,005 A | * | 11/1981 | Mutzhas | 607/94 |
| 5,742,066 A | * | 4/1998 | Cavesrti | 250/504 R |
| 5,905,268 A | * | 5/1999 | Garcia et al. | 250/504 R |
| 5,959,306 A | * | 9/1999 | Kalley et al. | 250/504 R |
| 5,997,154 A | * | 12/1999 | Cooper et al. | 362/293 |
| 6,177,678 B1 | * | 1/2001 | Brass et al. | 250/461.1 |

FOREIGN PATENT DOCUMENTS

| | | | | |
|---|---|---|---|---|
| JP | 8-128916 A | * | 5/1996 | G01M/3/38 |
| WO | WO 98/20365 A | * | 5/1998 | G01T/1/161 |

* cited by examiner

*Primary Examiner*—Constantine Hannaher
*Assistant Examiner*—Albert Gagliardi
(74) *Attorney, Agent, or Firm*—John R. Benefiel

(57) ABSTRACT

A light source and method for leak detection in which a dichroic filter is used with a powerful lamp emitting UV radiation. The dichroic filter is coated with layers of either tantalum pentoxide or hafnium dioxide to transmit UV in the approximate range of 340–380 nm and infrared above about 700 nm, while reflecting all visible light and shorter wavelength UV radiation.

3 Claims, 2 Drawing Sheets

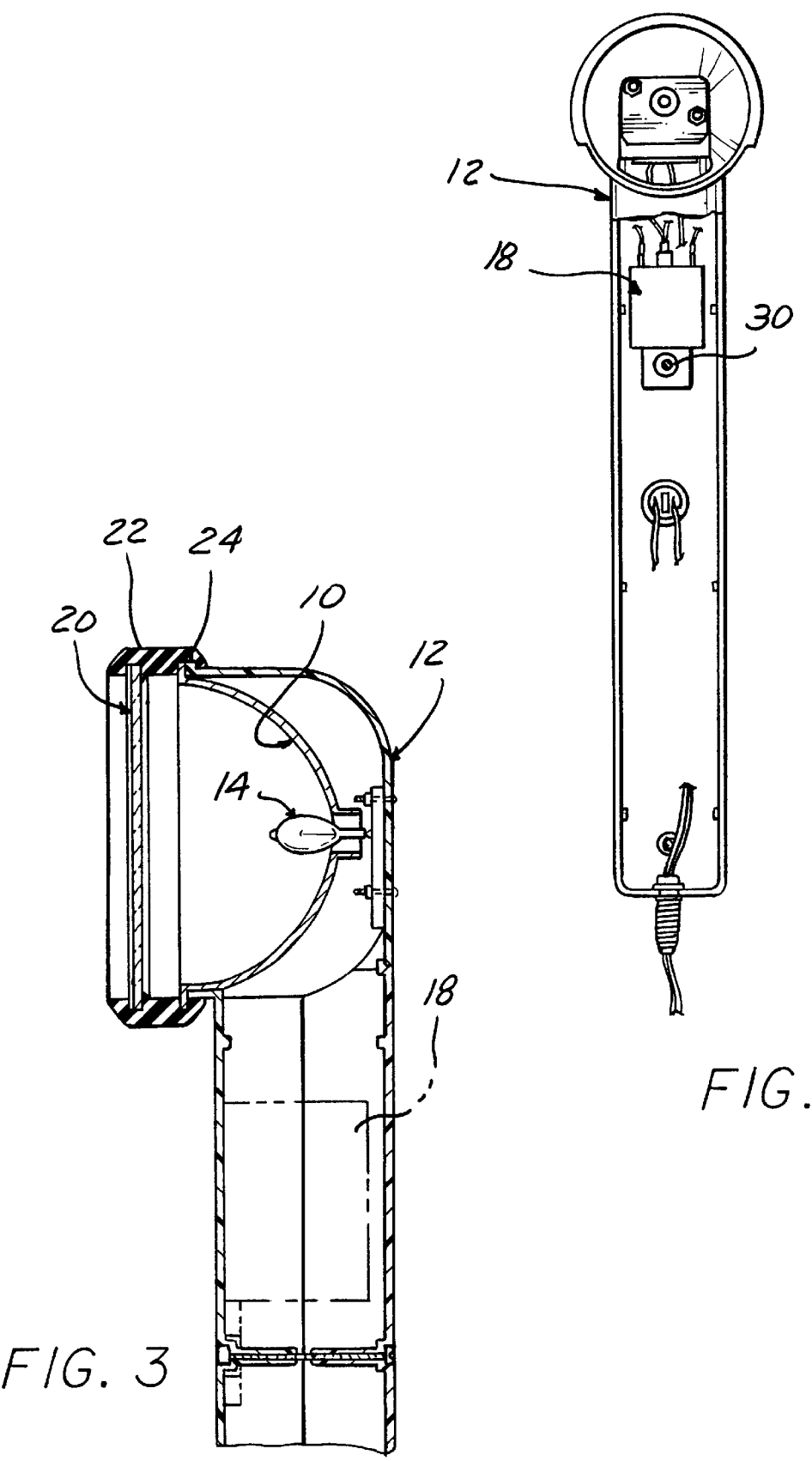

LIGHT SOURCE AND METHOD FOR CARRYING OUT LEAK DETECTION INSPECTIONS

CROSS REFERENCE TO RELATED APPLICATIONS

This invention is a continuation-in-part of U.S. Ser. No. 08/964,839, filed Nov. 5, 1997.

BACKGROUND OF THE INVENTION

This invention concerns lights for illuminating potential leak sites in air conditioning and refrigeration equipment, for both building and automotive applications, as well as for detecting fluid leaks in other sealed systems such automotive radiators, transmissions, crankcases, etc. It has been known to use fluorescing dyes, typically mixed with lubricants, and injected into the sealed equipment. If any of the dye leaks out at potential leak sites, the dye will fluoresce when illuminated and thus be easily detected by a technician who can thereby find any leaks that exist.

These dyes will fluoresce when illuminated with light and the light emitted from such dyes is in the visible range. Typical dyes used for this purpose fluoresce in this manner when illuminated with ultraviolet light and also in visible blue wavelengths.

For this reason, light sources have been developed which are intended to generate ultraviolet light of wavelengths ranging from about 300 nm to over 400 nm in the near UV or visible blue range. See U.S. Pat. No. 5,905,268 for an example of such a light, in which dichroic filters are used to prevent transmission of visible light other than blue light used to excite the dye. These filters rely on an interference reflection phenomenon as described in that patent.

The visibility of the resulting light emission to an observer is somewhat lessened by the presence of the visible blue light in the light beam emanating from the source, as this light reflects from the surfaces and reduces the contrast of any light emitted from the fluorescent dye.

This has led to the need to use "blue blocker" eyeglasses, which block out the blue light reflected from the surfaces around the potential leak sites when illuminating the same with the examining light. See copending U.S. application Ser. No. 08/964,834, filed on Nov. 5, 1997, and U.S. Pat. No. 5,674,000, issued Oct. 2, 1997.

When "deep" UV radiation is present, i.e., substantially under 340 nm wavelengths, a potential safety hazard is created in that such short wavelengths could be reflected so as to harm the eyes of the technician performing the inspection.

This safety hazard is also avoided by the "blue blocking" eyewear which is also designed to block UV radiation.

The requirement to use eyewear when conducting inspections is a disadvantage as it requires an extra item of equipment, and entails the inconvenience of finding and putting on the eyewear when conducting inspections.

It is the object of the invention to provide a light source and method for carrying out such leak detection inspections which eliminates the need for using blocking eyewear to increase the contrast of the fluorescent light emissions or to protect the eyes from deep UV radiation.

Another poorly understood problem with the use of dichroic blue filters of the type cited in U.S. Pat. No. 5,905,268 is that in fact there is poor transmission of UV by most of these filters. The Balzar AGB46 Dicholight filter described in the patent as having a transmission characteristic peaking on the UV range in fact does not transmit UV appreciably. It is believed that the reason for this poor UV transmission is the selection of coating material, such as titanium oxide.

While the interferences set up by the coating thicknesses can be calculated to pass or absorb any given range of wavelengths, the coating material itself will characteristically absorb particular wavelengths.

The end result is to preclude use of a pure "black" light, created by such a dichroic filter, as little dye exciting light will be produced by the light.

Accordingly, another object of the present invention is to provide a light source for the leak detection field which generates a light beam of substantially pure UV light by using a dichroic filter having a UV transmitting characteristic which enables a beam of powerful intensity when compared to other lights using dichroic filters commonly used for this application.

SUMMARY OF THE INVENTION

The present invention contemplates mounting a dichroic or reflecting type filter which is coated with a number of alternating layers, preferably alternately with tantalum pentoxide and silicon dioxide or with hafnium dioxide and silicone dioxide of a thickness suitable to cause interference reflection of "deep" UV light, i.e., shorter than 340 nm, and also of visible light, (over 380 nm up to 720 nm). Such coatings are preferably applied by ion assisted deposition.

Techniques producing reflection of these wavelengths by interference are well known to those skilled in the art.

A UV anti-reflection coating of magnesium fluoride on the outer surface of the filter further improves UV transmission.

Wavelengths over 720 nm are transmitted to eliminate infrared heating of the filter or other components.

A high power light source which emits UV radiation is used in conjunction with the dichroic filter.

DESCRIPTION OF THE DRAWINGS

FIG. 3 is a partially broken away view of the light of FIG. 1.

FIG. 4 is an enlarged fragmentary view in partial section of the head portion of the light of FIG. 1.

DETAILED DESCRIPTION

Figure 1:
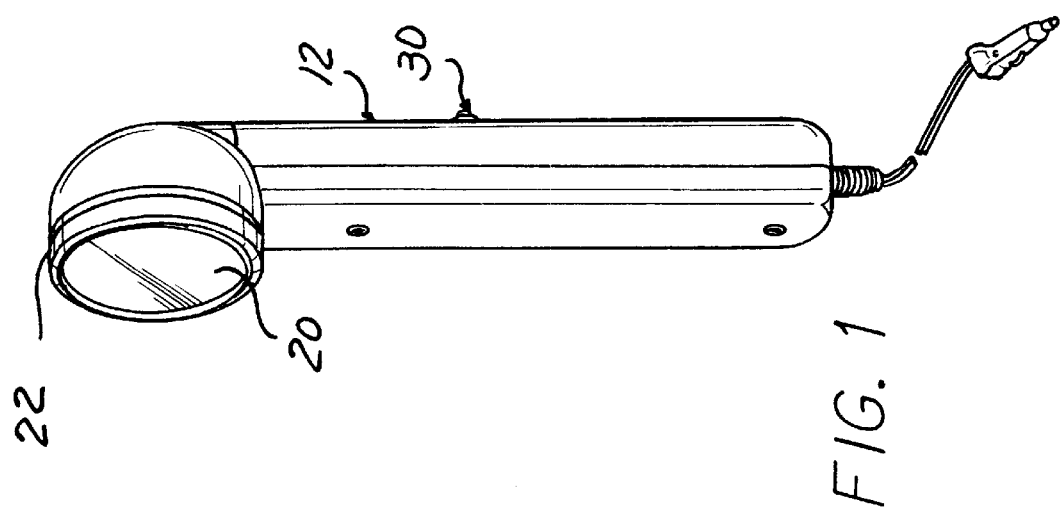
FIG. 1 is a perspective view of a light according to the present invention.
Figure 2:
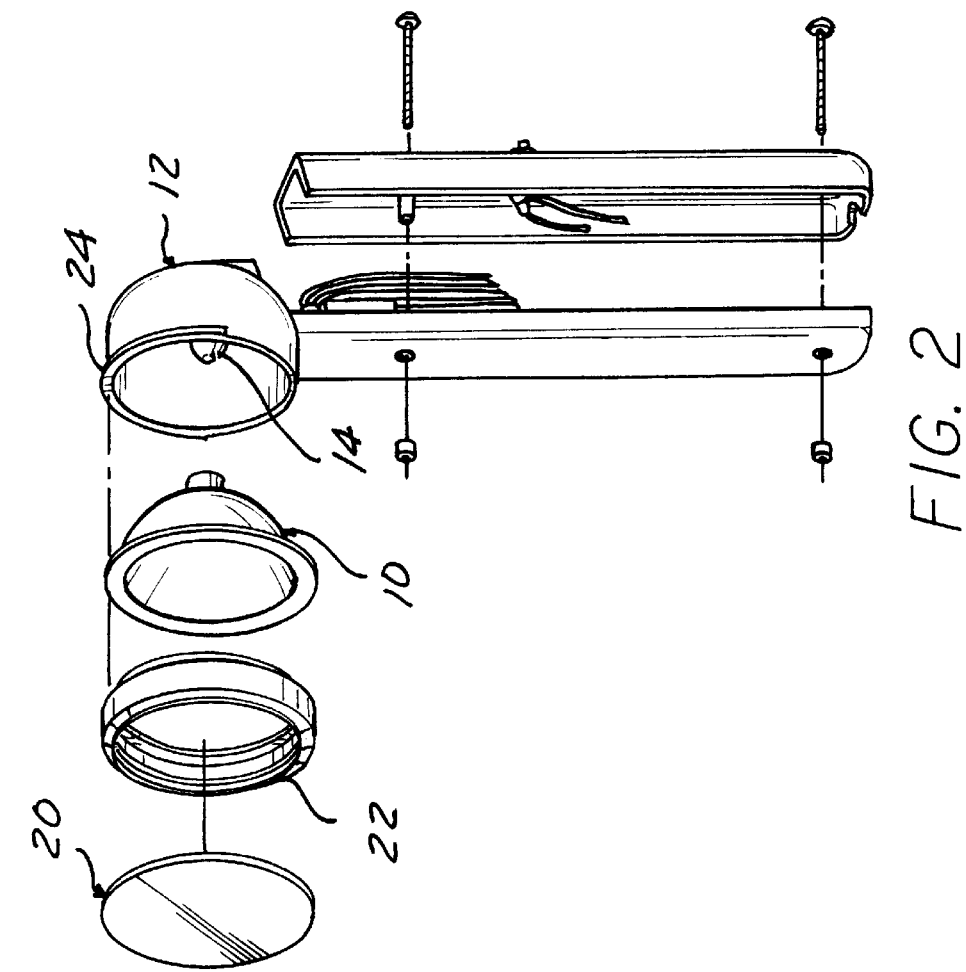
FIG. 2 is an exploded perspective view of the components of the light shown in FIG. 1.

In the following detailed description, certain specific terminology will be employed for the sake of clarity and a particular embodiment described in accordance with the requirements of 35 USC 112, but it is to be understood that the same is not intended to be limiting and should not be so construed inasmuch as the invention is capable of taking many forms and variations within the scope of the appended claims.

Referring to the drawing figures, the system according to the present invention uses a portable ultraviolet light source not unlike a flashlight, which includes a parabolically shaped reflector 10 mounted in a housing 12, which in turn mounts a lamp 14 located approximately at the focal point of the parabolic shape.

The lamp 14 is preferably a Xenon lamp of high color temperature (3500K), which produces substantial long wave ultraviolet light emissions. The envelope is made of quartz which is itself highly transmitive to long wave ultraviolet light.

The lamp 14 is also relatively compact allowing it to be placed at the focal point of the parabolic shape of the reflector 12.

A suitable bulb is available as part number FCR64625HLX from Osram Sylvania.

The parabolic reflector 12 is precision electroformed of nickel on an accurately shaped stainless steel mandrel.

A focal point of 0.187 inches allows the lamp 14 to be approximately located at the focal point of the parabolic to maximize beam concentration.

The lamp 14 is powered by a suitable power supply 16 which may consist of a transformer, reducing 110V AC (or 220V AC) to 12V.

A 12 volt dc power supply such as an auto battery may also be used in the well known manner.

The lamp 14 draws 100 watts of power such that a relatively high power source will be required, substantially greater than that required for a typical flashlight. Preferably, a relay 18 operated by a normally off spring biased switch 30 is used to turn the lamp 14 on and off, to minimize the on time of the lamp 14.

The reflecting surface 18 is the parabolic reflector 12 has a double layer of coatings, which are designed to eliminate the destructive interference caused by refraction of the interface of each media through which the light passes in being reflected from the surface 18. Refraction of short wavelength ultraviolet light would normally cause a phase difference to develop between the incident and reflective light beam, setting up a destructive interference and reducing the intensity of the reflected ultraviolet light.

The surface is given coatings, one of aluminum and one of silicon dioxide. The interface of silicon dioxide and air, and silicon dioxide and aluminum produces a double refraction in an opposite sense, which offset each other to eliminate the potential destructive interference which otherwise could occur.

The first coating is of aluminum, while the second coating is of silicon. The thickness of the silicon dioxide should be uniform and accurately held to achieve this effect, the thicknesses determined by the "quarter wave stack" principle.

The refractive index of each interface, i.e., the silicon dioxide and air, silicon dioxide and aluminum determines the effective phase shift of the reflected light. A thickness of aluminum of 0.057 microns and of silicon dioxide of 0.066 microns has been successfully used for this purpose. The silicon dioxide-air interface causes an approximate 13 degree forward phase shift, the silicon dioxide-aluminum interface a 13 degree lagging phase shift, thereby offsetting each other.

Silicon dioxide coatings have heretofore been employed simply to protect the substrate from scratches and oxidation but have not been sufficiently uniform nor of the proper thickness to achieve enhanced reflection of ultraviolet wavelengths.

A coated parabolic reflector suitable for this use is available from American Galvano, 312 N. Cota St., Unit I, Corona, Calif. 91720.

A dichroic filter 20 is held in a molded plastic mounting piece 22 snap fit to flange 24 is another component of the system of the present invention which is mounted to receive the ultraviolet beam emanating from the lamp 12 and the parabolic surface 18.

The filter 20 is designed to eliminate the visible light components of the light emanating from the lamp 12 and reflector 14, as well as the "deep UV" below 340 nm.

Filters blocking visible light have been employed in the past but have typically been designed to absorb visible light to prevent its transmittance. This results in excessive heating of the lens when used with high intensity light sources, making it vulnerable to cracking or shattering, as when contacted with water drops due to rapid cooling of localized areas of the glass.

Coatings are applied which cause reflection of the visible light ranges rather then absorbence, greatly reducing heating of the lens 20.

The filter 20 itself is preferably of borosilicate glass, commercially available as "Pyrex" (™), which has a very low coefficient of thermal expansion to thus minimize cracking from thermal shock.

The fluorescing dyes typically used for leak detection have an excitation range of ultraviolet light of wavelengths peacking around 365 nm. When excited by such ultraviolet light, fluorescing light of 495 nm to is emitted.

According to the concept of the present invention, deep UV below 340 nm is not transmitted as well as all visible light. That is, average transmittance is equal or greater while being less than 1% at 410–720 nm and great from 300 to 340 nm than 70% from 340 to 380 nm.

Light over 720 nm is in the invisible infrared range, which is allowed to be transmitted out of the confined space through the filter 20 to avoid overheating of the light 10, particularly the filter 20.

As discussed above, coatings which transmit UV light are essential when only UV light is transmitted for excitation purposes.

Such coating material may comprise preferably layers of tantalum pentoxide alternating with layers of silicon dioxide, applied by ion assisted deposition, a process known in the art.

Another suitable coating material is hafnium dioxide alternating with silicon dioxide.

Either of these coating systems will transmit a great proportion of UV light in the 340–380 nm range and are suitable.

Using the "quarterwave stack" principle developed by H. A., MacLeod, (see *Thin Film Optical Filter*, McGraw-Hill 1989), two layers of high and low refractive indices may be stacked to cause reflection of wavelengths only from 410 nm to 700 nm, allowing transmission of wavelengths from 340 nm to 380 nm and 720 nm to 1300 nm.

Other coatings may be applied in various thicknesses, such as magnesium fluoride, which may also be applied to the other surface of the borosilicate to eliminate any reflection of UV light.

This technique is used to create a bandwidth of light reflected from the filter above 380 nm extending approximately to 700 nm.

A suitable reflecting-transmitting filter lens for this purpose is commercially available as a "black light" dichroic filter from:

Z, C & R Coatings for Optics, Inc.
1250 E. 223$^{rd}$ Street
Suite 111
Carson, Calif. 90745

Thus, a powerful ultraviolet illuminating light source is provided, and the fluorescent light generated thereby is highly visible due to the elimination of reflected visible light, blocked by the filter 20.

This, in turn, makes leak detection inspections much easier and more reliable at relatively brightly lit sites.

What is claimed is:

1. In a method of detecting leaks from a sealed system including the steps of illuminating fluorescing fluid material which fluoresces when illuminated by ultraviolet light and viewing visible light emitted in response to illumination thereby by ultraviolet light in order to detect the presence of said fluorescing material at a potential leak site of said sealed system into which said fluorescing fluid material has been introduced, the improvement comprising the steps of:

generating an intense beam of ultraviolet light of wavelengths causing said material to fluoresce, including the step of energizing a high wattage ultraviolet lamp of a substantially higher wattage than a conventional flashlight to cause said ultraviolet emitting lamp to emit an intense beam of ultraviolet emitting light;

transmitting ultraviolet light from said lamp through a dichroic filter mounted in a housing supporting said ultraviolet emitting lamp, light of an approximate wavelength range of 340 to 380 nm while reflecting back visible light of wavelengths longer than said UV range and also UV light below said UV range, said dichroic filter also transmitting infrared light;

directing said intense ultraviolet beam at said site of possible leakage of fluid material.

2. The method according to claim 1 wherein in said coating step, tantalum pentoxide is employed as a coating material on said dichroic filter.

3. The method according to claim 1 wherein in said coating steps hafnium dioxide is employed as a coating material.

* * * * *

UNITED STATES PATENT AND TRADEMARK OFFICE
CERTIFICATE OF CORRECTION

PATENT NO.   : 6,362,488 B1
DATED        : March 26, 2002
INVENTOR(S)  : Robert Cabrera et al.

It is certified that error appears in the above-identified patent and that said Letters Patent is hereby corrected as shown below:

Column 3,
Line 42, after "is of silicon" insert -- dioxide --.

Column 4,
Line 21, delete "peacking" insert therefor -- peaking --.
Line 22, after "fluorescing light" delete "of" insert therefor -- around --.
Line 22, after "495 nm" delete "to".
Line 26, after "410-720 nm" delete "and great".
Line 27, after "nm" (first occurrence) insert -- , and greater --.

Column 5,
Line 19, delete "emitting".

Signed and Sealed this

Third Day of September, 2002

Attest:

Attesting Officer

JAMES E. ROGAN
Director of the United States Patent and Trademark Office